(12) United States Patent
Tanenbaum et al.

(10) Patent No.: US 10,379,660 B2
(45) Date of Patent: Aug. 13, 2019

(54) INPUT DEVICE FOR A MEDICAL TREATMENT SYSTEM

(71) Applicant: Fresenius Medical Care Holdings, Inc., Waltham, MA (US)

(72) Inventors: Lee Daniel Tanenbaum, Walnut Creek, CA (US); Aleo Nobel Mok, Orinda, CA (US); Haryono Dianto, Orange, CA (US); Mario Gumina, Danville, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 131 days.

(21) Appl. No.: 14/744,615

(22) Filed: Jun. 19, 2015

(65) Prior Publication Data
US 2016/0370911 A1    Dec. 22, 2016

(51) Int. Cl.
| | |
|---|---|
| *A61M 1/16* | (2006.01) |
| *G06F 3/041* | (2006.01) |
| *G06F 3/0482* | (2013.01) |
| *G06F 3/023* | (2006.01) |
| *G06F 3/01* | (2006.01) |

(Continued)

(52) U.S. Cl.
CPC ......... *G06F 3/0416* (2013.01); *A61M 1/1601* (2014.02); *G06F 3/018* (2013.01); *G06F 3/0233* (2013.01); *G06F 3/0482* (2013.01); *G06F 3/0488* (2013.01); *G16H 40/63* (2018.01); *G06F 19/3481* (2013.01)

(58) Field of Classification Search
CPC .... A61M 1/1601; G06F 3/0416; G06F 3/018; G06F 3/0233; G06F 3/0482; G06F 3/0488

USPC ......................................................... 210/85
See application file for complete search history.

(56) References Cited

U.S. PATENT DOCUMENTS

| | | | |
|---|---|---|---|
| 2007/0112603 A1 | 5/2007 | Kauthen et al. | |
| 2007/0235376 A1* | 10/2007 | Daniel | A61M 1/16 210/138 |

(Continued)

FOREIGN PATENT DOCUMENTS

| | | |
|---|---|---|
| WO | WO9835747 A1 | 8/1998 |
| WO | WO2007053683 A2 | 5/2007 |

(Continued)

OTHER PUBLICATIONS

WO2014033119 A1.*

(Continued)

*Primary Examiner* — Robert Clemente
*Assistant Examiner* — Akash K Varma
(74) *Attorney, Agent, or Firm* — Fish & Richardson P.C.

(57) ABSTRACT

A medical fluid treatment machine comprising: a pump configured to pump medical fluid to and from a patient; an input device configured to: display touch buttons, at least some of the touch buttons each representing a grapheme, and detect haptic interactions between a user and the touch buttons, wherein an interaction causes information related to the touch button to be received by the medical fluid treatment machine; and a control unit configured to control the input device, wherein controlling the input device includes causing the input device to switch between displaying i) a first set of touch buttons that correspond to a first language, and ii) a second set of touch buttons that correspond to a second language.

20 Claims, 7 Drawing Sheets

(51) Int. Cl.
*G06F 3/0488* (2013.01)
*G16H 40/63* (2018.01)
*G06F 19/00* (2018.01)

(56) References Cited

U.S. PATENT DOCUMENTS

| | | | | |
|---|---|---|---|---|
| 2008/0119731 | A1* | 5/2008 | Becerra | A61B 8/00 600/437 |
| 2009/0294339 | A1* | 12/2009 | Biewer | A61M 1/28 210/85 |
| 2012/0313858 | A1* | 12/2012 | Park | G06F 3/0238 345/171 |
| 2013/0172806 | A1 | 7/2013 | Griessmann et al. | |
| 2013/0317837 | A1 | 11/2013 | Ballantyne et al. | |
| 2014/0040810 | A1* | 2/2014 | Haliburton | G06F 3/017 715/773 |
| 2014/0121845 | A1 | 5/2014 | Mueller | |

FOREIGN PATENT DOCUMENTS

| | | | | |
|---|---|---|---|---|
| WO | WO 2007/053683 | * | 10/2007 | G09G 5/00 |
| WO | WO 2009058936 A1 | * | 5/2009 | G06F 19/3406 |
| WO | WO2009058936 A1 | | 5/2009 | |
| WO | WO 2009/058936 | * | 7/2009 | G06F 19/00 |
| WO | WO2014033119 A1 | | 3/2014 | |
| WO | WO2014033119 A1 | * | 6/2014 | G06F 19/00 |
| WO | WO2014105755 A1 | | 7/2014 | |
| WO | WO2014151669 A3 | | 10/2014 | |

OTHER PUBLICATIONS

WO 2007/053683, Kalathil et al.*
WO 2009/058936, Sandoe et al.*
WO 2009058936, Alvarez, May 2009.*
Notification of Transmittal of the International Search Report and the Written Opinion of the International Searching Authority for corresponding PCT Application No. PCT/US2016/036575, dated Oct. 24, 2016, 18 pages.

* cited by examiner

INPUT DEVICE FOR A MEDICAL TREATMENT SYSTEM

TECHNICAL FIELD

This disclosure relates to an input device (e.g., a keyboard) for a medical treatment system.

BACKGROUND

Dialysis is a treatment used to support a patient with insufficient renal function. Dialysis machines typically include input devices that can be used by nurses or doctors to input information related to treatment into the dialysis machine.

SUMMARY

In one aspect, a medical fluid treatment machine includes a pump configured to pump medical fluid to and from a patient. The medical fluid treatment machine also includes an input device configured to display touch buttons. At least some of the touch buttons each represent a grapheme. The input device is also configured to detect haptic interactions between a user and the touch buttons. An interaction causes information related to the touch button to be received by the medical fluid treatment machine. The medical fluid treatment machine also includes a control unit configured to control the input device. Controlling the input device includes causing the input device to switch between displaying i) a first set of touch buttons that correspond to a first language, and ii) a second set of touch buttons that correspond to a second language.

Implementations can include one or more of the following features.

In some implementations, the medical fluid treatment machine is a dialysis machine.

In some implementations, the medical fluid treatment machine is a hemodialysis machine.

In some implementations, controlling the input device includes causing the input device to display one or more touch buttons that each corresponds to a function related to a medical fluid treatment.

In some implementations, the functions related to the medical fluid treatment include one or more of starting the pump, stopping the pump, and adjusting the flow rate of the pump.

In some implementations, controlling the input device includes causing the input device to display one or more touch buttons that each corresponds to a link that is associated with a control screen that is displayed by the medical fluid treatment machine.

In some implementations, the input device is configured to display a touch button that causes the input device to switch between displaying the first set of touch buttons and the second set of touch buttons In some implementations, the input device is configured to display a touch button that causes the input device to display one or both of: i) one or more touch buttons that each corresponds to a function related to a medical fluid treatment, and ii) one or more touch buttons that each corresponds to a link that is associated with a control screen that is displayed by the medical fluid treatment machine.

In some implementations, the input device is configured to display a touch button that causes the input device to display one or more touch buttons that form a keyboard layout.

In some implementations, the keyboard layout is a QWERTY keyboard layout.

In some implementations, the functions related to the medical fluid treatment include one or more of starting the pump, stopping the pump, controlling the flow rate of the medical fluid flowing to or from the patient, starting a dialysis treatment, and ending a dialysis treatment.

In some implementations, the input device includes a drawing pad configured to receive a haptic graphical input.

In some implementations, the input device displays a region that defines the drawing pad.

In some implementations, the control unit is configured to receive information related to the haptic graphical input. The control unit is also configured to associate the haptic graphical input with a grapheme.

In some implementations, associating the haptic graphical input with a grapheme includes comparing the haptic graphic input to a database of graphical information.

In some implementations, the grapheme associated with the haptic graphical input is a symbol or character.

In some implementations, the symbol or character is a symbol or character of a non-English language.

In some implementations, the symbol or character is a logogram.

In another aspect, an input device includes a control unit configured to interpret touch input data received from a display screen of the input device, the touch input data based on detection of touch on a surface of the display screen. The control unit is also configured to transmit elements of control data to the display screen. The elements of control data are respectively capable of representing at least one of one or more functions related to a dialysis treatment, one or more graphemes that correspond to a first language, and one or more graphemes that correspond to a second language. The display screen is configured to receive elements of control data. The display screen is also configured to, based on the elements of control data, display one or more touch buttons that correspond to the one or more functions related to the dialysis treatment, at a first point in time, display one or more touch buttons that correspond to the one or more graphemes that correspond to the first language, at a second point in time, display one or more touch buttons that correspond to the one or more graphemes that correspond to the second language, and generate the touch input data based on detection of touch on a surface of the display screen.

In another aspect, an input device includes a display screen configured to display one or more touch buttons based on control data. The display screen is also configured to generate touch input data based on detection of touch on a surface of the display screen. The input device also includes a control unit configured to interpret touch input data received from the display screen. The control unit is also configured to transmit control data to the display screen. The control data represents one or more functions related to a dialysis treatment, at a first point in time, one or more graphemes that correspond to a first language, and at a second point in time, one or more graphemes that correspond to a second language.

Implementations can include one or more of the following advantages. In some implementations, the touch screen keyboard is configured to quickly and easily change between displaying touch buttons that correspond to a first language (e.g., English) and displaying touch buttons that correspond to a second language (e.g., a symbol-based language). Thus, the medical fluid treatment machine is not limited to input of only one language. Further, the medical fluid treatment machine does not need to be equipped with a particular keyboard based on the region in which the medical fluid treatment machine is to be used.

In some implementations, the touch screen keyboard's dynamic characteristics allow the touch screen keyboard to modify the display of touch buttons based on a number of conditions. For example, the touch screen keyboard may automatically display particular touch buttons in response to a condition (e.g., an alarm condition) of the medical fluid treatment machine. The touch screen keyboard may also restrict the user from interacting with particular touch buttons under certain conditions. For example, if the medical fluid treatment machine is expecting a numerical input, the touch screen keyboard may display only touch buttons that correspond to numerical digits. Similarly, if the medical fluid treatment machine is expecting an input that has a finite number of permissible values, the touch screen keyboard may display only touch buttons that correspond to the permissible values.

In some implementations, the use of the touch screen keyboard can promote cleanliness and sterilization, thereby reducing the risk of facilitating the spread of infection. Cleanliness and sterilization can be especially important in a medical environment due to the fragile health of the patients. In some implementations, the touch screen keyboard is substantially flat. The lack of ridges, raised sections, and crevices (e.g., spaces between keys of a traditional keyboard) allows for a user to easily and quickly clean the touch screen keyboard. A user can apply a cleaning agent to the touch screen keyboard and quickly wipe it off. Cleaning a traditional keyboard in this manner can be difficult, time consuming, and ineffective in part because the cleaning agent, which is often liquid, can settle between the keys and cause sticking and/or malfunction.

Other aspects, features, and advantages of the invention will be apparent from the description and drawings, and from the claims.

DETAILED DESCRIPTION

At various points before, during, or after a medical fluid treatment such as a dialysis treatment, medical personnel may need to input information into a dialysis machine. For example, before treatment, a nurse may input patient parameters, such as a Patient ID. The nurse may also input medical treatment information, such as information related to the patient's treatment prescription. The information related to the patient's treatment prescription can include dialysate parameters and a concentrate selection.

The medical fluid treatment systems (e.g., dialysis systems) described herein can include an input device for controlling functions of a medical fluid treatment machine (e.g., a dialysis machine). For example, the input device could be a touch screen keyboard. A touch screen keyboard is any device that presents touch buttons to a user on a display panel. A touch button is a portion of the display panel that, when invoked by a user (e.g., touched), causes the touch screen keyboard to communicate a control signal to another portion of the dialysis machine. Some of the touch buttons can represent one or more graphemes (e.g., letters, symbols, characters, digits, punctuation, etc.), and the user can interact with a touch button to cause information related to the associated grapheme to be received by the dialysis system as an input.

The touch screen keyboard can be customizable such that it is capable of presenting graphemes of various languages. For example, the touch screen keyboard may have a default appearance and mode of operation of a traditional English QWERTY keyboard. Upon receiving an instruction (e.g., from the dialysis system or from a user), the touch screen keyboard can present touch buttons that represent graphemes of another language rather than the default QWERTY layout. In this way, the touch screen keyboard is capable of displaying graphemes and receiving inputs in various languages.

In some implementations, the touch screen keyboard includes a drawing pad for receiving a graphical input. In cases in which the language presented by the touch screen keyboard is a symbol-based language, the touch screen keyboard may be unable to display every symbol associated with the language. Thus, a user can draw a symbol on the drawing pad to be received by the touch screen keyboard and the dialysis system. The symbol can be recognized by the touch screen keyboard and converted it into an input that can be understood by the dialysis system.

The touch screen keyboard may be capable of presenting touch buttons that correspond to specific dialysis functions. In some implementations, a secondary portion of the touch screen keyboard is designated for the display of such dialysis touch buttons. In some implementations, a primary portion of the touch screen keyboard (e.g., the portion that displays the graphemes associated with the selected language) may be dimensionally adjusted so as to define a secondary portion of the touch screen keyboard. The touch buttons in the secondary portion of the keyboard can perform functions such as starting/stopping the blood pump, controlling the dialysate flow rate, controlling the blood pump rate, and starting a new dialysis treatment, among others.

The use of the touch screen keyboard—as opposed to a keyboard with physical keys—can promote cleanliness and sterilization, thereby reducing the risk of facilitating the spread of infection. Cleanliness and sterilization can be especially important in a medical environment (e.g., a dialysis environment such as a dialysis clinic) due to the fragile health of the patients. In some implementations, the touch screen keyboard is substantially flat. The lack of ridges, raised sections, and crevices (e.g., spaces between physical keys of another kind of keyboard) allows for a user to easily and quickly clean the touch screen keyboard. For example, a user can apply a cleaning agent to the touch screen keyboard and quickly wipe it off. Cleaning a traditional keyboard in this manner can be difficult, time consuming, and ineffective in part because the cleaning agent, which is often liquid, can settle between the keys and cause sticking and/or malfunction.

Figure 1:
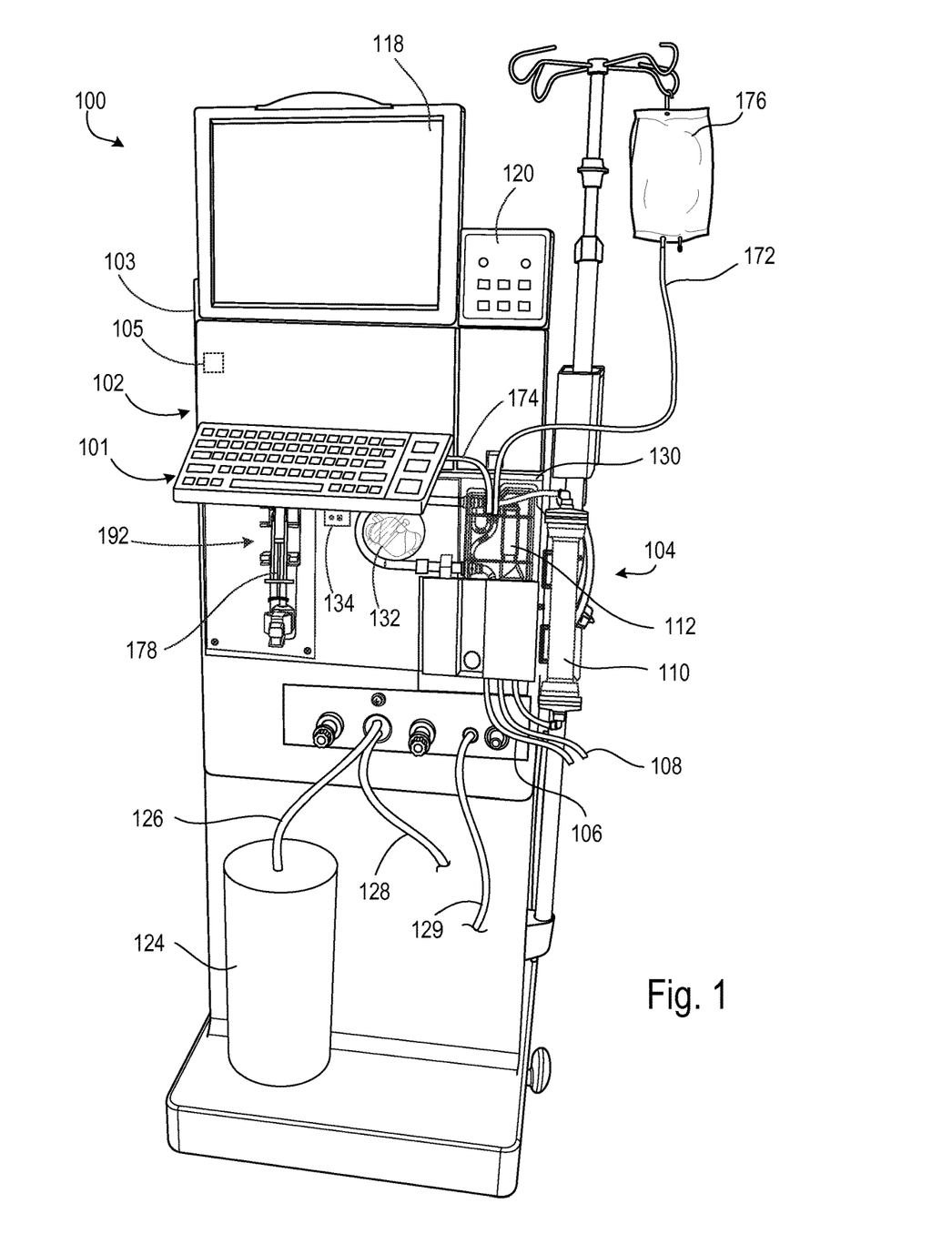
FIG. 1 is a front perspective view of a hemodialysis system, including a touch screen keyboard.

Referring to FIG. 1, a hemodialysis system 100 includes a hemodialysis machine 102 to which a disposable blood component set 104 that forms a blood circuit is connected.

As described below, the hemodialysis system 100 includes a touch screen keyboard 101.

In general, during hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing 103 of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a self-sealing vent assembly that allows air to pass therethrough while inhibiting (e.g., preventing) liquid from passing therethrough. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As will be described in greater detail below, this arrangement facilitates control of the flow of blood through the blood circuit and monitoring of the blood flowing through the blood circuit.

The blood pump 132 can be controlled by a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

Still referring to FIG. 1, the hemodialysis machine 102 includes a keyboard (e.g., a touch screen keyboard 101), a touch screen 118, and a control panel 120. The touch screen keyboard 101, the touch screen 118, and the control panel 120 allow the operator to input data, e.g., various different treatment parameters, to the hemodialysis machine 102 and to control the hemodialysis machine 102. In addition, the touch screen keyboard 101 and the touch screen 118 serve as displays to convey information to the operator of the hemodialysis system 100.

The hemodialysis machine 102 includes a control unit 105 (e.g., a processor such as a microprocessor or microcontroller) that resides inside the machine and which is configured to communicate with the touch screen keyboard 101, the touch screen 118, and the control panel 120. The control unit 105 is configured to receive data from the touch screen keyboard 101, the touch screen 118, and the control panel 120 and control the hemodialysis machine 102 based on the received data.

Figure 2A:
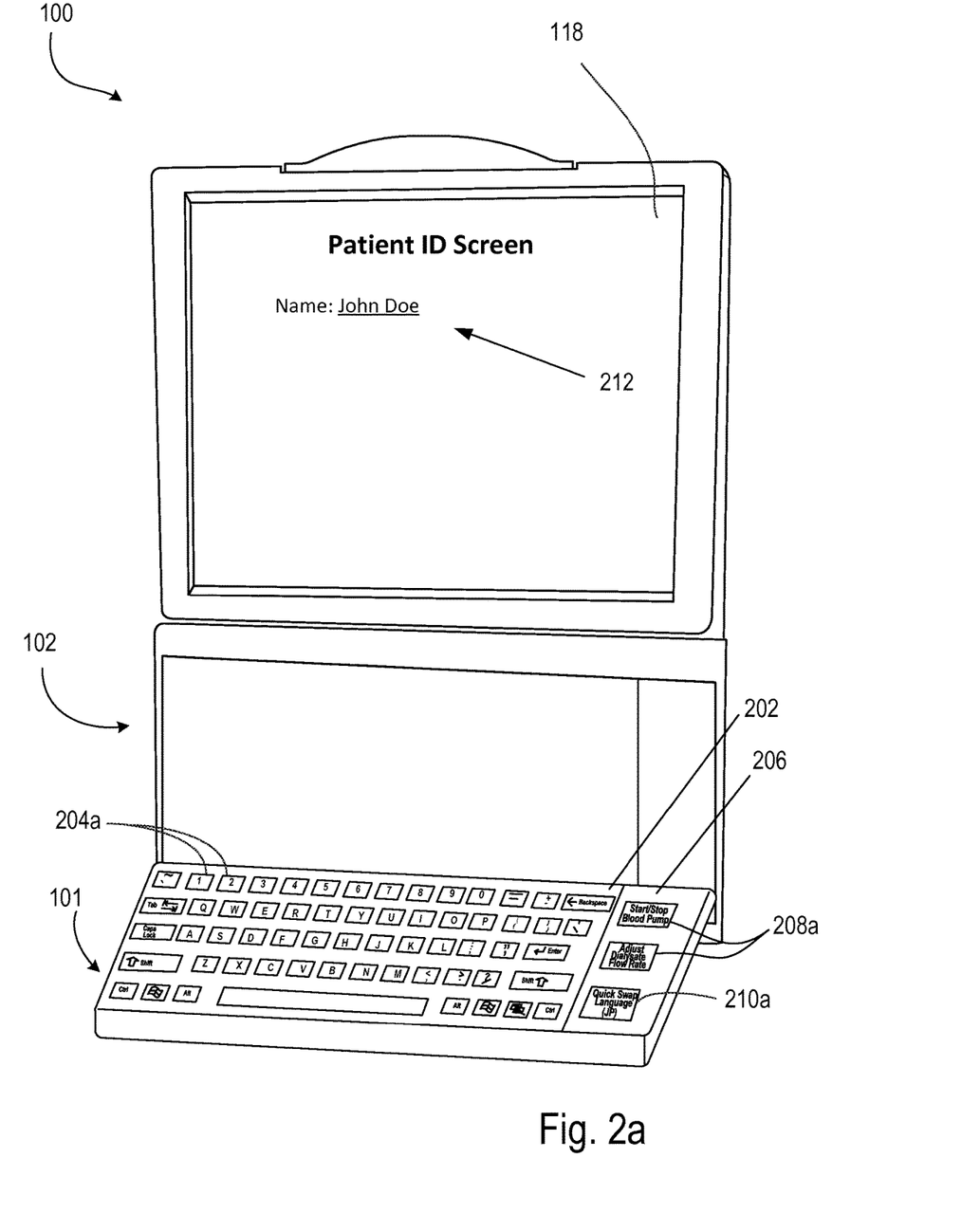
FIG. 2a is an example of the touch screen keyboard displaying touch buttons that correspond to the English language.

FIG. 2a shows an example of the touch screen keyboard 101 in which the touch screen keyboard 101 has a standard English QWERTY configuration that is commonly used in physical keyboards. In this example, the touch screen keyboard 101 has a first display region 202 and a second display region 206. Each of the display regions 202, 206 is configured to display one or more touch buttons 204a, 208a. The control unit 105 is configured to control the touch screen keyboard 101 to cause the touch screen keyboard 101 to display the touch buttons 204a, 208a. The control unit 105 transmits elements of control data to the touch screen keyboard 101 to cause the touch screen keyboard 101 to display particular touch buttons. Some of the touch buttons 204a, 208a each represent one or more graphemes. A grapheme is a unit used in describing the writing system of a language, and can include letters, symbols, characters, digits, and punctuation, among others. In some examples, a grapheme is a symbol or character that represents a word (e.g., a logogram). In some examples, a grapheme is a syllabic character (e.g., Japanese kana). In some examples, a grapheme corresponds to a sound, such as a sound that is spoken in a particular language (e.g., a phoneme). In some examples, a grapheme corresponds to a concept, and the concept can be associated with a glyph that represents the concept. In this example, the touch buttons 204a, 208a take the form of touch button keys (e.g., 204a) or touch button functions (e.g., 208a). The touch buttons keys 204a in the first display region 202 are representations of keys of a standard English QWERTY keyboard. The touch buttons keys 204a correspond to the English language. The touch button functions 208a in the second display region 206 correspond to functions that can be performed by the hemodialysis machine 102. The touch button functions 208a are typically displayed in at least the same language as the language that corresponds to the touch button keys 204a.

The control unit 105 interprets touch input data that is based on detection of touch on the surface of the touch screen keyboard 101. For example, the touch screen keyboard 101 can detect haptic interactions between a user and the touch buttons 204a, 208a. A haptic interaction is an interaction that involves touch (e.g., contact). An interaction (e.g., a tap initiated by the user) causes information related to the particular touch button to be received by the control unit 105 of the hemodialysis machine 102. In some examples, a user may want to enter patient identification information into the hemodialysis machine 102. The touch screen 118 may display a field related to the patient (e.g., a "Name" field 212). When the user taps the "J" touch button key, the control unit 105 receives information indicating that a "J" is being received as input. The control unit 105 may then send a signal to the touch screen 118 to cause the touch screen to display the received input. In some examples, the user may want to cause the hemodialysis machine 102 to perform a function related to a dialysis treatment. When the user taps the "Start/Stop Blood Pump" touch button function 208a, the control unit 105 receives information indicating that an instruction to perform the particular function is being received. The control unit 105 may then send one or more control signals to components of the hemodialysis machine 102 to effectuate the dialysis function (e.g., to start or stop the blood pump 132).

Figure 2B:
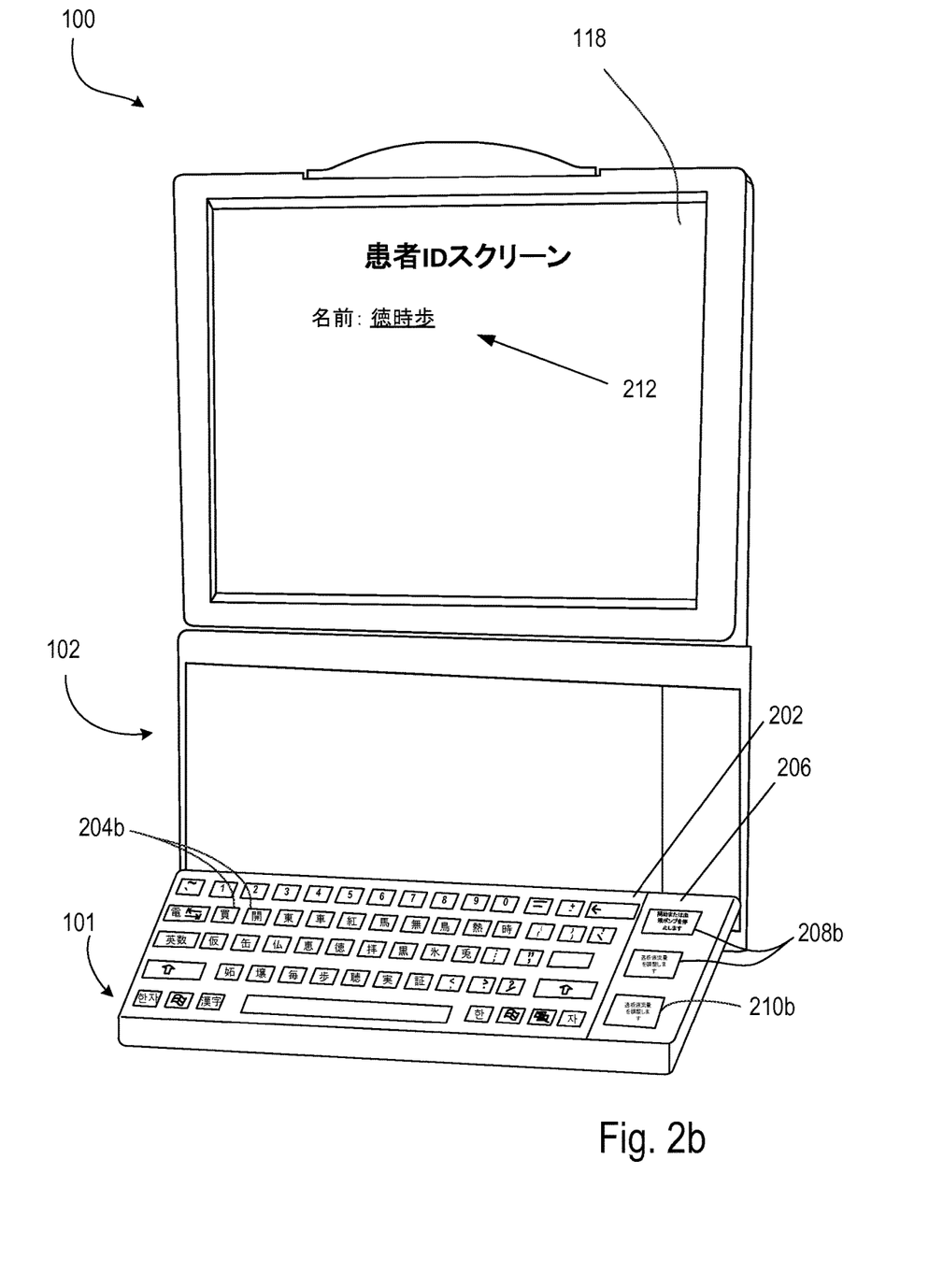
FIG. 2b is an example of the touch screen keyboard displaying touch buttons that correspond to a non-English language.

The control unit 105 is also configured to cause the touch screen keyboard 101 to switch between displaying a first set of touch buttons that correspond to a first language (e.g., the English touch buttons 204a, 208a of FIG. 2a) and a second set of touch buttons that correspond to a second language. FIG. 2b shows the touch screen keyboard 101 with an alternative Japanese configuration. In this example, the control unit 105 is causing the touch screen keyboard 101 to display a second set of touch buttons 204b, 208b that are in Japanese.

The control unit 105 can receive an instruction to cause the touch screen keyboard 101 to switch between displaying the first set of touch buttons and the second set of touch buttons. In some implementations, the instruction can be received in response to the user accessing a setting of the hemodialysis machine 102 and selecting a language in which the touch buttons are to be displayed. The hemodialysis machine 102 may include a number of built-in languages that the touch screen keyboard 101 is capable of displaying touch buttons in. In some implementations, the control unit 105 causes the touch screen 118 to display text in the same language as that of the touch buttons. For example, as shown in FIG. 2b, the touch screen 118 may display the "Patient ID Screen" and the "Name" field 212 in Japanese.

The set of touch buttons displayed by the touch screen keyboard 101 can include a "Quick Swap" touch button 210a, 210b which, when invoked, causes the touch screen keyboard 101 to switch from displaying the first set of touch buttons to displaying the second set of touch buttons. The languages associated with the sets of touch buttons may be set by the user, and may be a language that is often used to input information. In the example shown in FIGS. 2a and 2b, the "Quick Swap" touch button 210a, 210b causes the touch screen keyboard 101 to switch between displaying in English and Japanese.

In some implementations, the hemodialysis machine 102 is configured to receive information related to additional languages, and the control unit 105 can process the information to cause the touch screen keyboard 101 to display touch buttons in one of the additional languages. In some implementations, the information related to the additional languages can be received over a network (e.g., the Internet) that the hemodialysis machine 102 is in communication with.

Figure 3A:
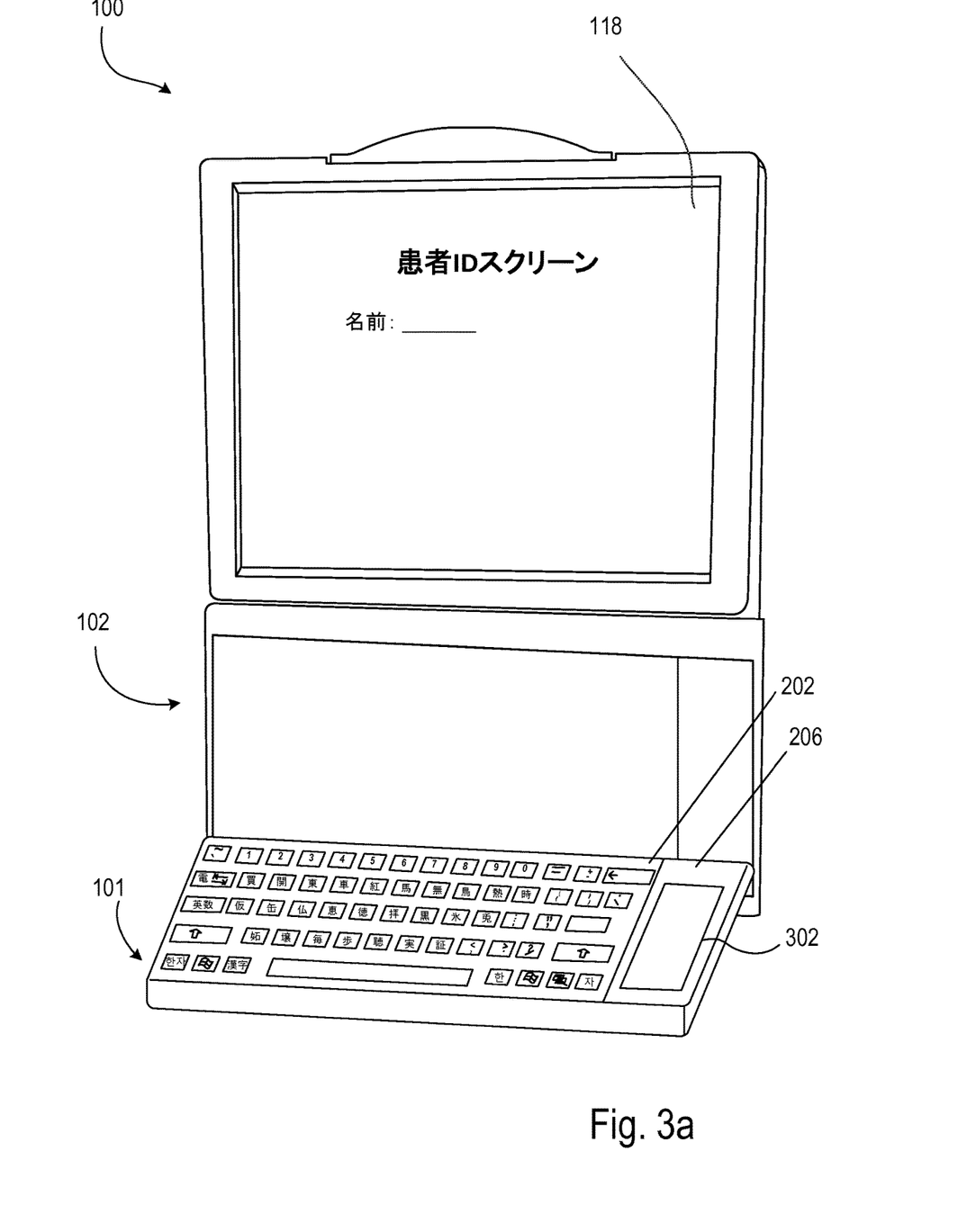
FIGS. 3a and 3b show an example of the touch screen keyboard displaying a drawing pad.
Figure 3B:
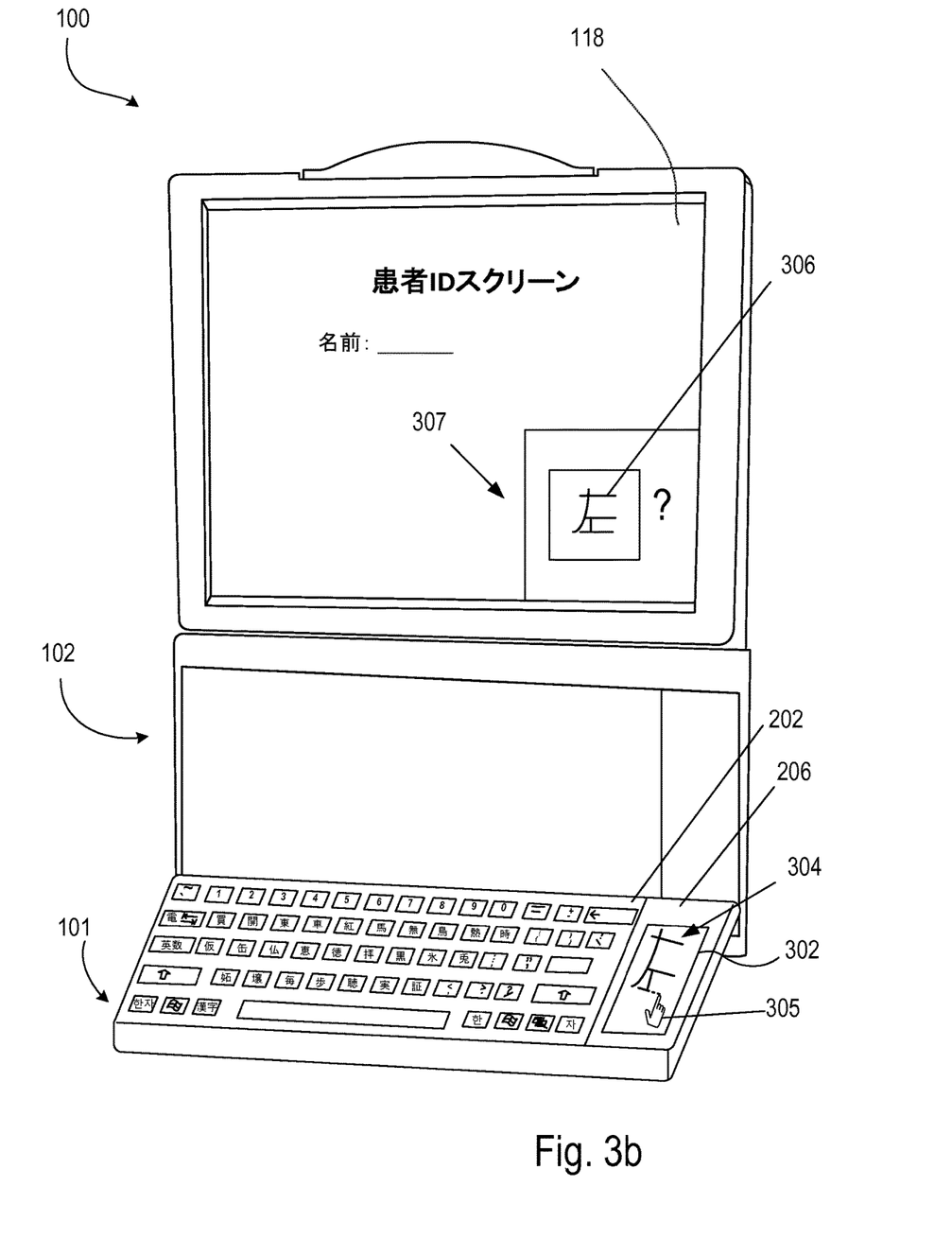

FIGS. 3a and 3b show an example of the touch screen keyboard 101 in which the touch screen keyboard 101 includes a drawing pad 302 in the second display region 206. The drawing pad 302 is configured to receive a haptic graphical input from the user and associate the haptic graphical input with a grapheme. In cases in which the language presented by the touch screen keyboard 101 is a non-English symbol-based language such as Japanese, as shown in FIGS. 3a and 3b, the touch screen keyboard 101 may be unable to display every symbol associated with the language, e.g., due to the large number of possible symbols. For example, Japanese is typically written in a mixture three writing systems—kanji, hiragana, or katakana—each of which includes a large number of symbols. To accommodate a greater number of inputs, the touch screen keyboard 101 enables a user to draw a character, rather than display a separate key for each possible character. The user can draw a symbol 304 on the drawing pad 302 to be received by the touch screen keyboard 101 and the hemodialysis machine 102. The drawn symbol 304 can be recognized by the touch screen keyboard 101 and converted into an input that can be understood by the control unit 105. The symbol 304 may be a logogram that represents a Japanese word or phrase.

In some implementations, a library of known graphemes is stored on the hemodialysis machine 102. Referring to FIG. 3a, the user can draw a symbol 304 on the drawing pad 302 (e.g., using a finger, as represented by the hand 305, not drawn to scale). As the user draws the symbol 304, the control unit 105 compares aspects of the drawn symbol 304 to aspects of known symbols. If a correlation is identified, the control unit 105 indicates that it may have identified a known symbol 306 that is being received as input. In some implementations, the touch screen 118 displays the known symbol 306 that corresponds to the drawn symbol 304 when the control unit 105 identifies a potential correlation between the two. The potential correlation is represented in a confirmation region 307, which includes a question mark that indicates that confirmation is sought from the user. The user can indicate whether the potential correlation is correct (e.g., by interacting with the known symbol 306 displayed on the touch screen 118). In some implementations, known graphemes are stored in a database that the hemodialysis machine 102 is in communication with. For example, the control unit 105 may compare aspects of the drawn symbol 304 to aspects of known symbols that reside on a database that is accessible over a network (e.g., the Internet).

Figure 4A:
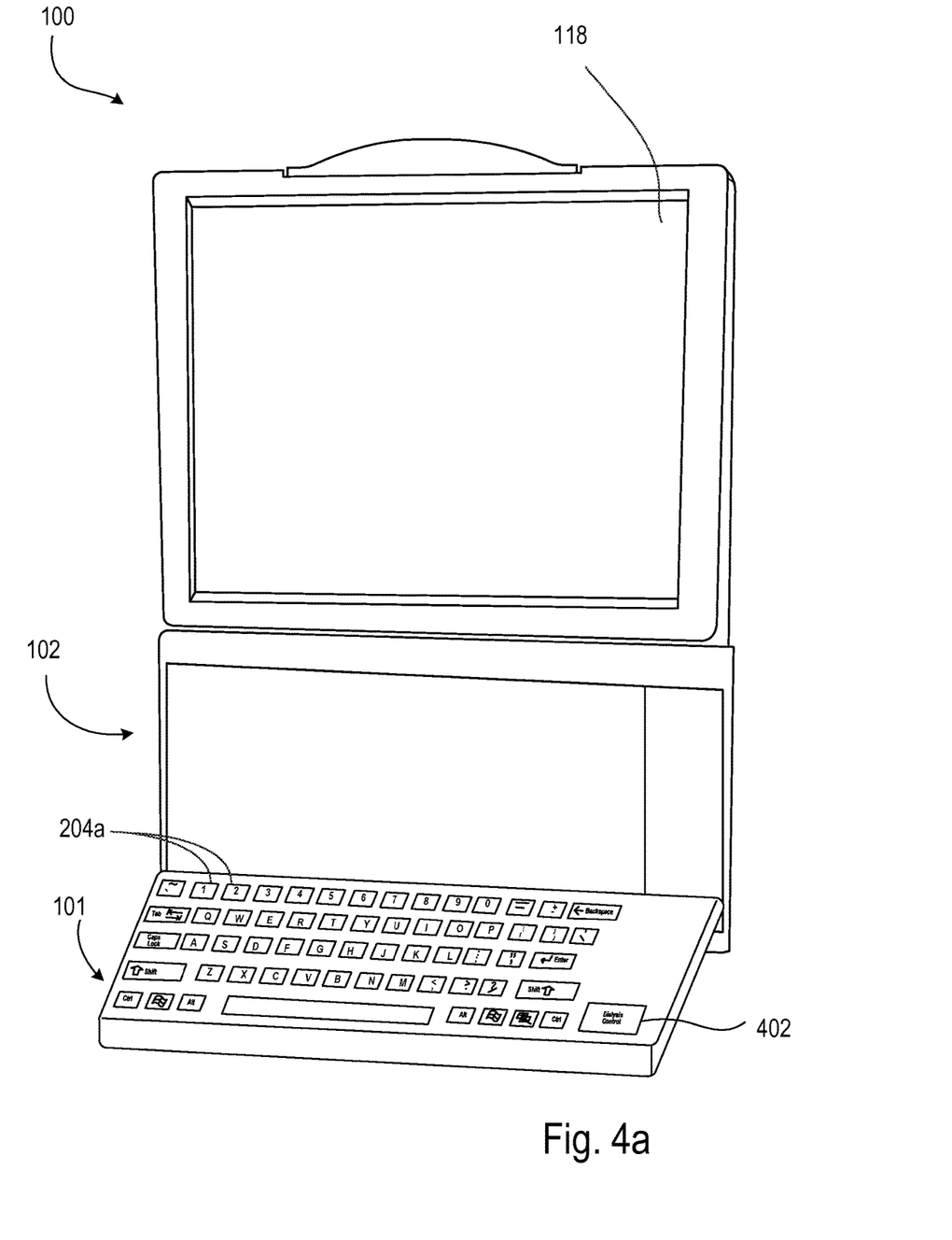
FIGS. 4a and 4b show an example of the touch screen keyboard displaying touch buttons for switching between display modes.
Figure 4B:
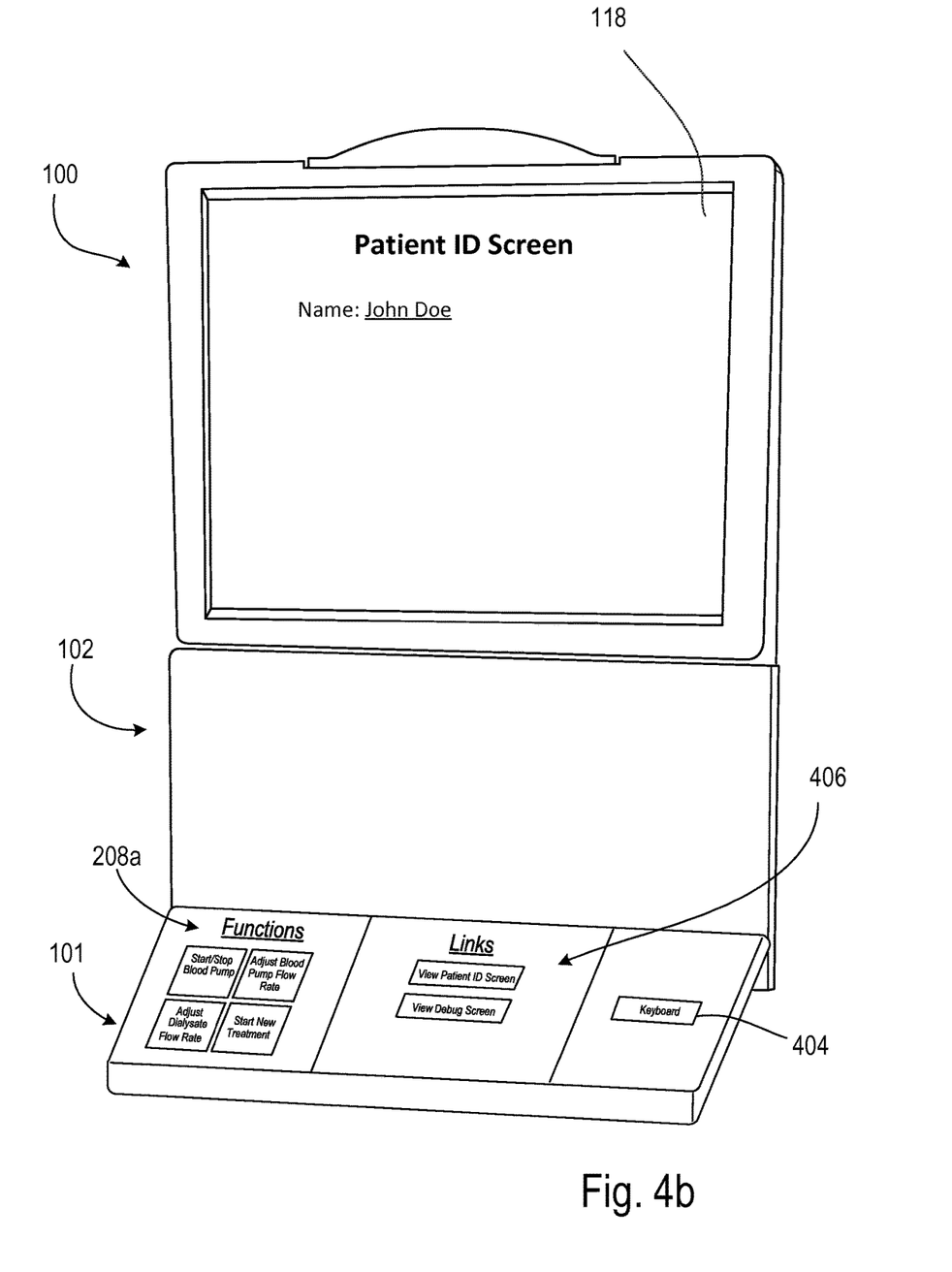

FIGS. 4a and 4b show an example of the touch screen keyboard 101 that includes a "Dialysis Control" touch button 402 and a "Keyboard" touch button 404, respectively, for switching between display modes. Rather than having multiple display regions that are concurrently displayed, the touch screen keyboard 101 can switch between displaying a first group of touch buttons that take the form of touch button keys (e.g., the touch button keys 204a of FIG. 4a) and a second group of touch buttons that include touch buttons that take the form of touch button functions (e.g., the touch button functions 208a of FIG. 4b) and touch buttons that take the form of links (e.g., the links 406 of FIG. 4b). When the user interacts with the "Dialysis Control" touch button 402, the control unit 105 causes the touch screen keyboard 101 to switch between displaying the first group of touch buttons and the second group of touch buttons.

Referring to FIG. 4b, the second group of touch buttons are displayed when the touch screen keyboard 101 is in a dialysis control mode. The dialysis control mode allows the user to easily access various control screens and cause the hemodialysis machine 102 to perform a number of dialysis functions. In the dialysis control mode, the touch screen keyboard 101 displays touch button functions 208a and links 406. The touch button functions 208a operate in the same manner as described above with reference to FIG. 2a. When the user interacts with one of the links 406, the touch screen 118 displays a control screen associated with the particular link 406. For example, the user can interact with the "View Patient ID Screen" link 406 to cause the touch screen 118 to display the Patient ID Screen.

The second group of touch buttons includes a "Keyboard" touch button 404 that causes the touch screen keyboard 101 to display the first group of touch buttons (e.g., the standard English QWERTY keyboard). Continuing with the example above, once the Patient ID Screen is displayed, the user can interact with the "Keyboard" touch button 404 to bring up the standard English QWERTY keyboard, and the user can input patient ID information in the manner described above.

A method of using the hemodialysis system 100 to administer a dialysis treatment to a patient will now be described. Before treatment begins, an English user (e.g., a caregiver such as a nurse or a doctor) enters information into the hemodialysis machine 102 via the touch screen keyboard 101. The caregiver typically begins by entering patient parameters into the touch screen keyboard 101. The caregiver also enters medical treatment information, such as information related to the patient's treatment prescription. The information related to the patient's treatment prescription can include dialysate parameters and a concentrate selection. During input of the patient parameters, the touch screen keyboard 101 may be in any of the configurations described above. During input of the patient's treatment prescription, the touch screen keyboard 101 may be in any of the configurations described above, although in some implementations, the caregiver may find it easier to access and input dialysis control information when the touch screen keyboard 101 is in the dialysis control mode (as shown in FIG. 4b). The treatment prescription can be analyzed by the hemodialysis machine 102 to determine appropriate operating parameters for the patient's treatment.

Once the patient parameters and the medical treatment information are entered, the caregiver prepares the patient for dialysis treatment. Referring back to FIG. 1, the arterial and venous patient lines 106, 108 are connected to the patient, and hemodialysis is initiated. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

During hemodialysis, the blood pump 132 is activated causing blood to circulate through the blood circuit. The blood is drawn from the patient via the arterial patient line 106 and flows to an arterial pressure sensor capsule. An arterial pressure sensor on the front face of the module 130 aligns with the pressure sensor capsule and measures the pressure of the blood flowing through the blood circuit on the arterial side. The blood then flows through a pump line, which is operatively engaged with the blood pump 132. From the pump line, the blood flows to the dialyzer 110. After exiting the dialyzer 110, the blood flows through a venous pressure sensor capsule where the pressure of the blood on the venous side is measured by an associated pressure sensor on the front face of the module 130.

Upon reviewing the arterial and venous pressure measurements, the caregiver may determine that the blood pump 132 needs to be stopped. The caregiver can stop the blood pump 132 by interacting with the "Start/Stop Blood Pump" touch button function 208a. If the touch screen keyboard 101 is in the configuration shown in FIG. 4a, the caregiver may first interact with the "Dialysis Control" touch button 402, and then interact with the "Start/Stop Blood Pump" touch button function 208a.

During administration of the dialysis treatment, the caregiver may want to enter additional patient parameters. If the touch screen keyboard 101 is in the dialysis control mode, the caregiver can interact with the "Keyboard" touch button 404 to cause the touch screen keyboard 101 to display the standard English QWERTY keyboard again.

At a later point in time, a second dialysis treatment may be initiated by a second caregiver. The second caregiver may speak only Japanese. Before treatment begins, the caregiver can interact with the "Quick Swap" touch button 210a (shown in FIG. 2a) to cause the touch screen keyboard to display a second set of touch buttons that are displayed in Japanese. The caregiver can then control the hemodialysis machine 102 in a manner similar to that described above.

At the conclusion of the treatment, the caregiver can clean the touch screen keyboard 101 to reduce the risk of facilitating the spread of potential infection. For example, the caregiver can apply a cleaning agent to the touch screen keyboard 101 and quickly and easily wipe it off.

While certain implementations have been described, other implementations are possible.

While the touch screen keyboard is shown as being in a particular position throughout the figures, in some implementations, the position of the touch screen keyboard is adjustable. For example, in some implementations, the touch screen keyboard can assume a position having an angle of between 0° and 90° relative to a front surface of the dialysis machine (e.g., where the touch screen keyboard is in a vertical, front-facing position when it is in the 0° position, and the touch screen keyboard is in a horizontal, up-facing position when it is in the 90° position).

While we described the drawing pad as being included in the touch screen keyboard when the language presented by the touch screen keyboard is a symbol-based language such as Japanese, the drawing pad can also be included when other languages (e.g., English) are presented. In some implementations, the drawing pad can identify gestures received as input from the user. Upon recognizing a gesture, the control unit can cause the hemodialysis machine to perform a particular function. In some implementations, recognizable gestures can include swipes and taps with one or more fingers of the user (e.g., tapping the drawing pad with two fingers, swiping across the drawing pad with two fingers, etc.). In some implementations, the caregiver can use the drawing pad to provide his or her signature or to receive a biometric input (e.g., a fingerprint).

In some implementations, the touch screen keyboard is configured to dynamically display touch buttons according to previous input received by the touch screen keyboard and/or the current state of the hemodialysis machine. In some implementations, the touch screen keyboard may disable (e.g., "grey out") certain touch buttons that correspond to inappropriate input. For example, if the caregiver is entering information that is numerical (e.g., a particular dialysate flow rate), the touch screen keyboard may display digits 0-9 in the form of a typical number pad. The number pad may provide numerical touch buttons that are larger than those included in other configurations. In some implementation, the touch screen keyboard may display only certain digits. For example, if there is a finite number of digits that would be valid for input, only those digits may be displayed as touch buttons.

In some implementations, the touch screen keyboard may automatically display touch button functions in response to an alarm condition of the hemodialysis machine. For example, the touch screen keyboard may be displaying the standard QWERTY keyboard when an alarm condition arises that requires attention from the caregiver. There may be a finite number of suitable responses to the alarm condition. The touch screen keyboard may display touch button functions that each corresponds to one of the suitable response, and the caregiver can choose which touch button function to interact with in order to cause the hemodialysis machine 102 to perform the associated function.

While we described the hemodialysis machine as including a touch screen, in some implementations, the hemodialysis machine includes a traditional monitor.

While we have described the touch screen keyboard being connected to a hemodialysis machine, the keyboard could alternatively be included in other types of medical treatment systems. Examples of other medical treatment systems in which the touch screen keyboard can be used include hemofiltration systems, hemodiafiltration systems, apheresis systems, cardiopulmonary bypass systems, and peritoneal dialysis systems.

Implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor (e.g., processing module), a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-transitory non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations have been described. Nevertheless, it will be understood that various modifications may be made without departing from the spirit and scope of the invention. Accordingly, other implementations are within the scope of the following claims.

What is claimed is:
1. A medical fluid treatment machine comprising:
a pump configured to pump medical fluid to and from a patient;
an input device configured to:
display a plurality of touch buttons that are configured to receive haptic input from a user, at least some of the touch buttons each representing a grapheme, wherein, in a first state, a first set of touch buttons each displays a grapheme of a first language, and wherein, in a second state, a second set of touch buttons each displays a grapheme of a second language;
display a language swap touch button that is configured to receive haptic input from the user, wherein i) in the first state, the language swap touch button displays a phrase indicating the second language to be applied to the at least some of the touch buttons, and ii) in the second state, the language swap touch button displays a phrase indicating the first language to be applied to the at least some of the touch buttons; and
detect the haptic input received from the user, wherein detecting the haptic input causes information related to the touch button to be received by the medical fluid treatment machine; and a control unit configured to cause the input device to toggle between displaying i) the first set of touch buttons, and ii) the second set of touch buttons in response to the user providing the haptic input to the language swap touch button, wherein a first haptic input provided to the language swap touch button causes the language swap touch button to switch from displaying the phrase indicating the second language to displaying the phrase indicating the first language and causes the toggling of the input device from displaying the first set of touch buttons to displaying the second set of touch buttons, and a second haptic input provided to the language swap touch button causes the language swap touch button to switch from displaying the phrase indicating the first language to displaying the phrase indicating the second language and causes the toggling of the input device from displaying the second set of touch buttons to displaying the first set of touch buttons.

2. The medical fluid treatment machine of claim 1, wherein the medical fluid treatment machine is a dialysis machine.

3. The medical fluid treatment machine of claim 1, wherein the medical fluid treatment machine is a hemodialysis machine.

4. The medical fluid treatment machine of claim 1, wherein the control unit is configured to cause the input device to display one or more touch buttons that each corresponds to a function related to a medical fluid treatment.

5. The medical fluid treatment machine of claim 4, wherein the functions related to the medical fluid treatment include one or more of starting the pump, stopping the pump, and adjusting a flow rate of the pump.

6. The medical fluid treatment machine of claim 1, wherein the control unit is configured to cause the input device to display one or more touch buttons that each corresponds to a link that is associated with a control screen that is displayed by the medical fluid treatment machine.

7. The medical fluid treatment machine of claim 1, wherein the input device is configured to display a touch button that causes the input device to display one or both of: i) one or more touch buttons that each corresponds to a function related to a medical fluid treatment, and ii) one or more touch buttons that each corresponds to a link that is associated with a control screen that is displayed by the medical fluid treatment machine.

8. The medical fluid treatment machine of claim 1, wherein the input device is configured to display a touch button that causes the input device to display one or more touch buttons that form a keyboard layout.

9. The medical fluid treatment machine of claim 8, wherein the keyboard layout is a QWERTY keyboard layout.

10. The medical fluid treatment machine of claim 7, wherein the functions related to the medical fluid treatment include one or more of starting the pump, stopping the pump, controlling a flow rate of the medical fluid flowing to or from the patient, starting a dialysis treatment, and ending a dialysis treatment.

11. The medical fluid treatment machine of claim 1, wherein the input device is configured to display a drawing pad that is configured to receive a haptic drawn input from the user.

12. The medical fluid treatment machine of claim 11, wherein the control unit is configured to:
receive information related to the haptic drawn input; and
associate the haptic drawn input with a grapheme.

13. The medical fluid treatment machine of claim 12, wherein associating the haptic drawn input with a grapheme includes comparing the haptic drawn input to a database of graphical information.

14. The medical fluid treatment machine of claim 12, wherein the grapheme associated with the haptic drawn input is a symbol or character.

15. The medical fluid treatment machine of claim 14, wherein the symbol or character is a symbol or character of a non-English language.

16. The medical fluid treatment machine of claim 14, wherein the symbol or character is a logogram.

17. An input device comprising:
a control unit configured to:
interpret touch input data received from a display screen of the input device, the touch input data based on detection of touch on a surface of the display screen; and
transmit elements of control data to the display screen, the elements of control data respectively capable of representing
one or more graphemes of a first language and
one or more graphemes of a second language; and
the display screen configured to receive elements of control data and, based on the elements of control data:
display a plurality of touch buttons that are configured to receive haptic input from a user, at least some of the touch buttons each representing a grapheme, wherein, in a first state, a first set of touch buttons each displays a grapheme of a first language, and wherein, in a second state, a second set of touch buttons each displays a grapheme of a second language;
display a language swap touch button that is configured to receive haptic input from the user, wherein i) in the first state, the language swap touch button displays a phrase indicating the second language to be applied to at least some of the touch buttons, and ii) in the second state, the language swap touch button displays a phrase indicating the first language to be applied to the at least some of the touch buttons;
toggle between displaying i) the first set of touch buttons, and ii) the second set of touch buttons in response to the user providing the haptic input to the language swap touch button; and
generate the touch input data based on the detection of touch on the surface of the display screen,
wherein a first haptic input provided to the language swap touch button causes the language swap touch button to switch from displaying the phrase indicating the second language to displaying the phrase indicating the first language and causes the toggling of the input device from displaying the first set of touch buttons to displaying the second set of touch buttons, and a second haptic input provided to the language swap touch button causes the language swap touch button to switch from displaying the phrase indicating the first language to displaying the phrase indicating the second language and causes the toggling of the input device from displaying the second set of touch buttons to displaying the first set of touch buttons.

18. An input device comprising:
a display screen configured to:
   display a plurality of touch buttons that are configured to receive haptic input from a user, at least some of the touch buttons each representing a grapheme, wherein, in a first state, a first set of touch buttons each displays a grapheme of a first language, and wherein, in a second state, a second set of touch buttons each displays a grapheme of a second language; and
   generate touch input data based on detection of touch on a surface of the display screen; and
a control unit configured to:
   interpret the touch input data received from the display screen; and
   transmit the control data to the display screen, the control data representing:
      a language swap function,
      one or more graphemes of a first language, and
      one or more graphemes of a second language;
   wherein:
   the language swap function is controlled by a language swap touch button that is configured to receive haptic input from the user, wherein i) in the first state, the language swap touch button displays a phrase indicating the second language to be applied to at least some of the touch buttons, and ii) in the second state, the language swap touch button displays a phrase indicating the first language to be applied to the at least some of the touch buttons; and
   the display screen is configured to toggle between displaying i) the first set of touch buttons, and ii) the second set of touch buttons in response to the user providing the haptic input to the language swap function,
   wherein a first haptic input provided to the language swap touch button causes the language swap touch button to switch from displaying the phrase indicating the second language to displaying the phrase indicating the first language and causes the toggling of the input device from displaying the first set of touch buttons to displaying the second set of touch buttons, and a second haptic input provided to the language swap touch button causes the language swap touch button to switch from displaying the phrase indicating the first language to displaying the phrase indicating the second language and causes the toggling of the input device from displaying the second set of touch buttons to displaying the first set of touch buttons.

19. The medical fluid treatment machine of claim 1, wherein the input device is configured to display a dialysis control touch button that is configured to receive haptic input from the user, wherein the control unit is configured to replace the touch buttons that represent graphemes with a plurality of touch buttons each corresponding to a dialysis function in response to the user providing the haptic input to the dialysis control touch button.

20. The medical fluid treatment machine of claim 1, wherein toggling between displaying the first set of touch buttons and the second set of touch buttons comprises switching between displaying the first set of touch buttons and displaying the second set of touch buttons.

* * * * *